United States Patent [19]

Kinami et al.

[11] Patent Number: 5,210,253

[45] Date of Patent: May 11, 1993

[54] FLUORINE-CONTAINING ORGANOSILICON COMPOUND

[75] Inventors: Hitoshi Kinami, Annaka; Kouichi Yamaguchi, Takasaki; Hideki Fujii, Annaka; Shuji Suganuma, Takasaki, all of Japan

[73] Assignee: Shin-Etsu Chemical Co., Ltd., Tokyo, Japan

[21] Appl. No.: 961,361

[22] Filed: Oct. 15, 1992

[30] Foreign Application Priority Data

Oct. 17, 1991 [JP] Japan .................. 3-298324

[51] Int. Cl.$^5$ .................. C07F 7/08; C07F 7/18
[52] U.S. Cl. .................. 556/448
[58] Field of Search .................. 556/448

[56] References Cited

U.S. PATENT DOCUMENTS

| | | | |
|---|---|---|---|
| 4,968,828 | 11/1990 | Yamamoto | 556/448 X |
| 4,996,344 | 2/1991 | Inomata et al. | 556/448 |
| 5,043,464 | 8/1991 | Yamamoto | 556/448 X |
| 5,099,053 | 3/1992 | Takaoka et al. | 556/448 |

Primary Examiner—Paul F. Shaver
Attorney, Agent, or Firm—Oblon, Spivak, McClelland, Maier & Neustadt

[57] ABSTRACT

Fluorine-containing organosilicon compound according to the present invention is expressed by the general formula:

$$Rf-R-Si(=CH_2)-(OCCH_3)_3$$

wherein Rf is a perfluoropolyether group having 3 to 17 carbon atoms, R is an alkylene group having 1 to 6 carbon atoms or a group of the general formula, $-R^2-O-R^3-$, wherein $R^2$ and $R^3$ may be the same or different and are each alkylene groups having 1 to 6 carbon atoms. The present compound is useful as a curing catalyst for organo-polysiloxane compounds that are condensation curable at room temperature. The compositions added with the fluorine-containing organosilicon compound have excellent characteristics such as water and oil repellencies, chemical resistance and contamination resistance and offer a variety of uses such as high performance sealing, coating and electric insulating materials.

7 Claims, 2 Drawing Sheets

FLUORINE-CONTAINING ORGANOSILICON COMPOUND

BACKGROUND OF THE INVENTION

1. Field of the Invention

The present invention relates to a novel organosilicon compound, and more particularly to a fluorine-containing organosilicon compound useful as a curing agent for organopolysiloxane compositions that are condensation curable at room temperature such as contamination resistant sealant.

2. Description of the Prior Art

Various compounds having a hydrolyzable group are known in the art as a curing agent for organopolysiloxane compositions that are condensation curable at room temperature.

It is also known that introduction of fluorine atoms into the organopolysiloxane improves water and oil repellencies, chemical resistance and contamination resistance of the resultant cured product such as silicone elastomer.

SUMMARY OF THE INVENTION

The present invention aims at providing a novel organosilicon compound which is useful as a curing agent for condensation curable organopolysiloxane compositions and which effectively improves water and oil repellencie, chemical resistance and contamination resistance of the resultant cured product because of fluorine. It also aims at providing a process of production thereof.

According to the present invention, there is provided a fluorine-containing organosilicon compound having the following general formula (I):

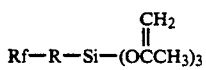
(I)

wherein Rf represents a perfluoropolyether group having 3 to 17 carbon atoms, and R represents an alkylene group having 1 to 6 carbon atoms, or a group expressed by the general formula: —R$^2$—O—R$^3$— wherein R$^2$ and R$^3$ may be the same or different and are each alkylene groups having 1 to 6 carbon atoms.

The present invention also provides a process for producing the fluorine-containing organosilicon compound of the general formula (I) which comprises the step of reacting acetone in the presence of a dehydrochlorinating agent with a fluorine-containing trichlorosilane of the general formula (II):

 (II)

wherein Rf and R are as above specified.

DETAILED DESCRIPTION OF THE INVENTION

Fluorine-Containing Organosilicon Compound

Figure 1:
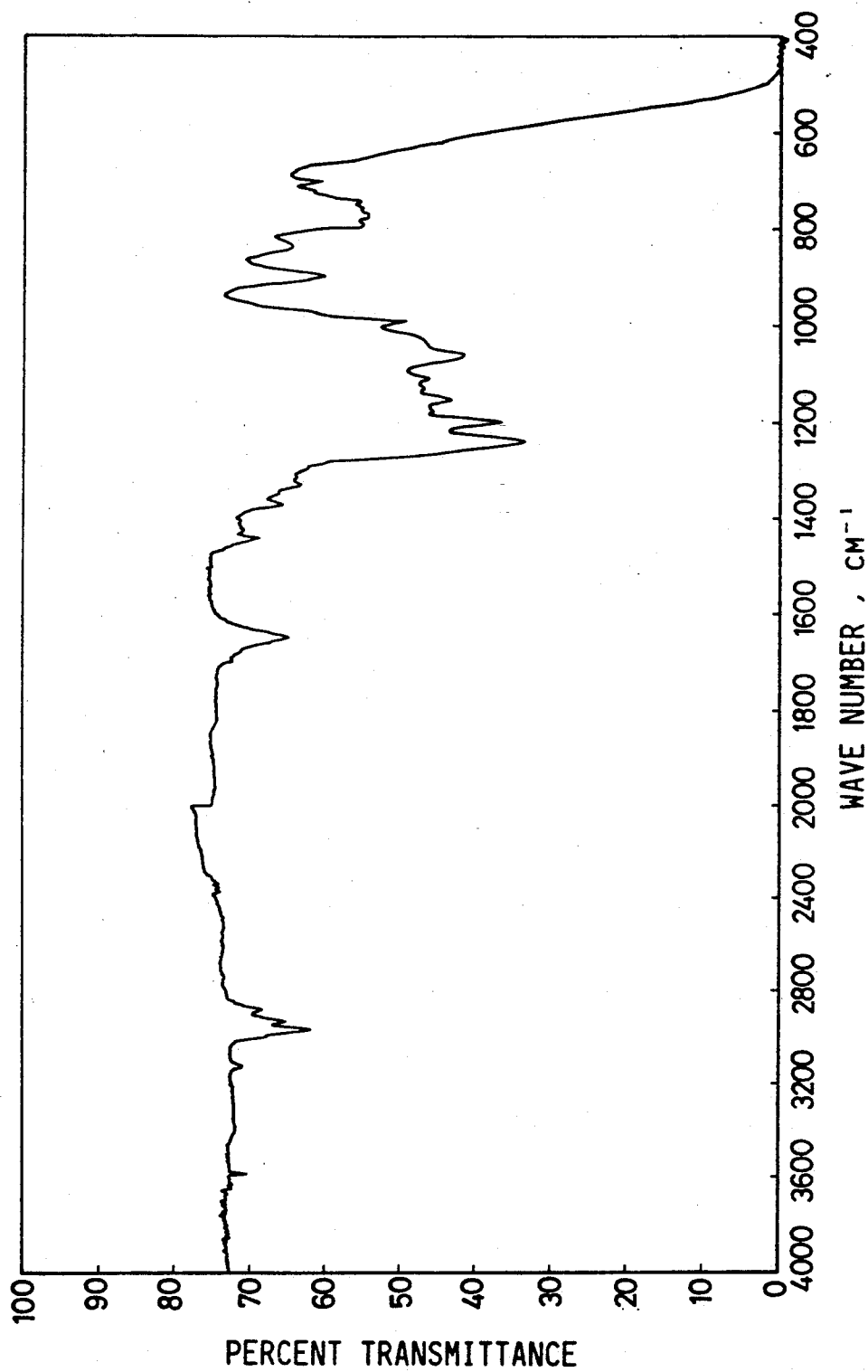
FIG. 1 shows an infrared absorption spectrum of the fluorine-containing organosilicon compound according to the Example 1 of the present invention.

In the general formula (I) representing the fluorine-containing organosilicon compound according to the present invention, Rf represents a perfluoropolyether group having 3 to 17 carbon atoms. Typical examples of the perfluoro-polyether group include:

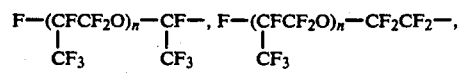

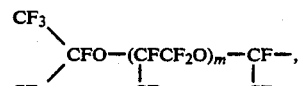

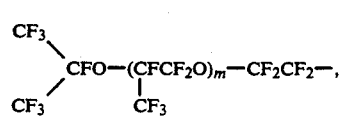

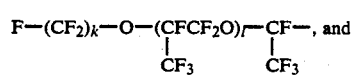

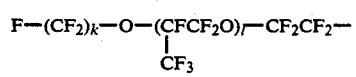

wherein n is an integer of from 1 to 5, m an integer of 0 or from 1 to 4, k an integer of from 1 to 12 and l an integer of from 1 to 7.

Typical examples of R which is a divalent radical include the following:

—CH$_2$CH$_2$—, —CH$_2$CH$_2$CH$_2$—,
—CH$_2$O—CH$_2$CH$_2$CH$_2$—,

Typical examples of fluorine-containing organosilicon compound of the general formula (I) include but are not limited to the following:

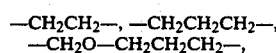

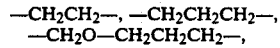

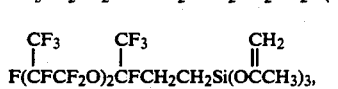

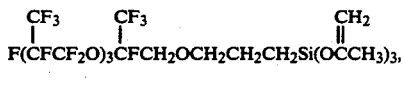

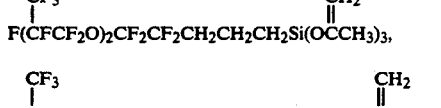

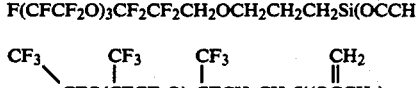

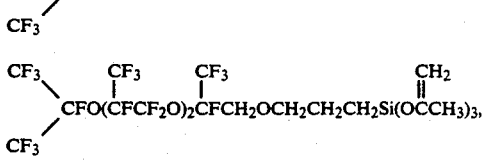

-continued

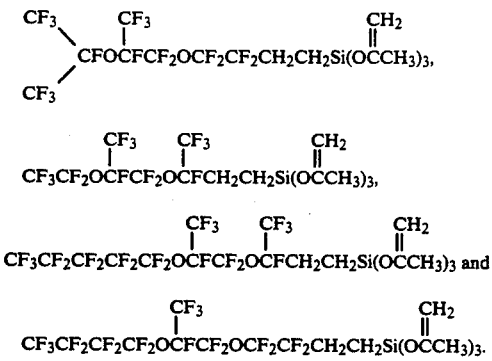

$$CF_3CF_2CF_2CF_2OCFCF_2OCF_2CF_2CH_2CH_2Si(OCCH_3)_3.$$
(with CF_3 and CH_2 substituents as shown)

The fluorine-containing organosilicon compound according to the present invention can be used for various purposes, and is particularly useful as a curing agent for organopolysiloxane compositions that are condensation curable at room temperature. Compositions added with said compound have superior properties such as water and oil repellencies, chemical resistance and contamination resistance because of the introduced fluorine-containing substituents and offer extensive uses such as high performance sealing, coating and electric insulating materials.

Process of Production

The fluorine-containing organosilicon compound of the present invention can be obtained by reacting in the presence of a dehydrochlorinating agent acetone and a fluorine-containing trichlorosilane of the general formula (II):

$$Rf-R-SiCl_3 \qquad (II)$$

wherein Rf and R are as defined above.

The amount of acetone per mol of the fluorine-containing trichlorosilane is preferably in the range of from 3.0 to 15.0 mol, more preferably from 6.0 to 12.0 mol.

The dehydrochlorinating agent to be used includes, for example, triethylamine, pyridine, dimethylaniline and diethylamine and is preferably used in the amount of from 3.0 to 6.0, more preferably from 3.3 to 4.5 mol per mol of the fluorine-containing trichlorosilane.

In reacting the fluorine-containing trichlorosilane with acetone as above mentioned, metal halides such as copper chloride, aluminum chloride and zinc chloride are preferably used as a catalyst to promote dehydrochlorination. The catalyst may be added in a so-called catalytic amount, but the generally preferred amount is in the range of from 0.001 to 0.1 mol and more preferably from 0.005 to 0.05 mol per mol of the fluorine-containing trichlorosilane. The reaction conditions are preferably adjusted on a case-by-case basis, but the generally preferable reaction temperature is in the range of from 20° to 150° C., and more preferably from 40° to 100° C. The reaction time may be in the range of from one to 50 hours, and more preferably from 5 to 20 hours.

EXAMPLES

Example 1

Into a 1000 ml four-necked flask, 350 g (6.0 mol) of acetone, 167 g (1.65 mol) of triethylamine and 0.8 g (8.0 mol) of cuprous chloride were charged. Into the flask was added dropwise with a dropping funnel over 30 minutes, 307 g (0.5 mol) of fluorine-containing trichlorosilane of the general formula (II'):

$$F-(CFCF_2O)_2-CFCH_2CH_2SiCl_3 \qquad (II')$$

Upon completion of the addition, the system was heated for 16 hours under stirring and reflux of acetone. The system was then filtered to remove amine hydrochloride to obtain a filtrate, which was concentrated, and distilled to obtain 192 g (yield, 56.5%) of a fraction having a boiling point of 128° C./13 mmHg.

The fraction thus obtained was subjected to IR spectrophotometry and NMR spectrophotometry. From the results below, it was confirmed that the fraction was a fluorine-containing organosilicon compound having the following structural formula (I'):

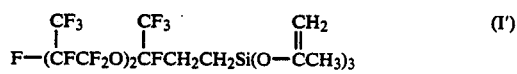

$$F-(CFCF_2O)_2CFCH_2CH_2Si(O-CCH_3)_3 \qquad (I')$$

IR spectrum: as shown in FIG. 1.

Characteristic absorption (>C=CH_2) 1650 cm$^{-1}$ $^1$H - NMR spectrum (solvent CCl_4, internal standard: CHCl_3)

| δ (ppm) | |
|---|---|
| 0.8–1.4 | (m, 2H, Si—CH_2—C) |
| 1.9 | (s, 9H, —C(=)—CH_3) |
| 2.0–2.7 | (m, 2H, Si—C—CH_2—) |
| 4.1–4.5 | (d, 6H, \C=CH_2 /) |

Example 2

Example 1 was repeated, except that in place of the fluorine-containing trichlorosilane used in Example 1, 245.8 g (0.5 mol) of a fluorine-containing trichlorosilane represented by the following formula:

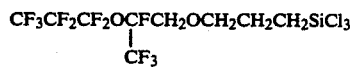

$$CF_3CF_2CF_2OCFCH_2OCH_2CH_2CH_2SiCl_3$$
(with CF_3 substituent)

was used, thereby obtaining 177.9 g of a fraction having a boiling point of 120° C./4 mmHg.

The fraction thus obtained was subjected to IR spectrophotometry and NMR spectrophotometry. From the results below, it was confirmed that the fraction was a fluorine-containing organosilicon compound having the following structural formula:

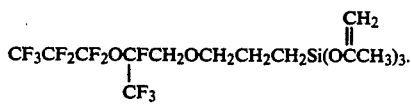

$$CF_3CF_2CF_2OCFCH_2OCH_2CH_2CH_2Si(OCCH_3)_3.$$
(with CF_3 and CH_2 substituents)

Yield: 64.0%

Figure 2:
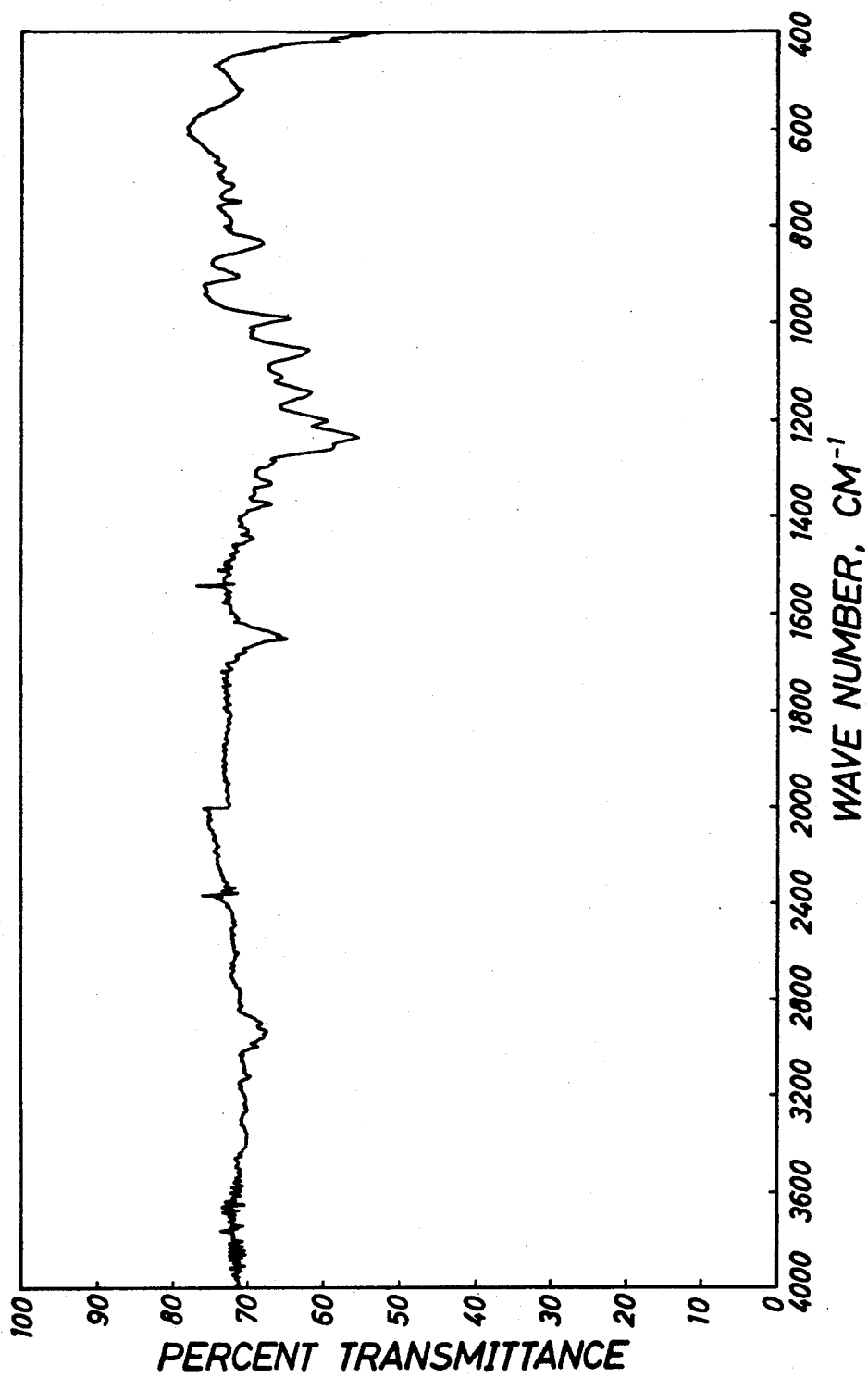
FIG. 2 shows an infrared absorption spectrum of the fluorine-containing organosilicon compound according to the Example 2 of the present invention.

IR spectrum: as shown in FIG. 2.

Characteristic absorption (>O=CH$_2$): 1650 cm$^{-1}$.
1H - NMR spectrum (solvent: CCl$_4$, internal standard: CHCl$_3$)

| δ (ppm) | |
|---|---|
| 0.8-1.1 | (m, 2H, —Si—CH$_2$—C) |
| 1.2-1.8 | (m, 2H, —Si—C—CH$_2$—) |
| 1.9 | (s, 9H, —C—CH$_3$—) |
| 3.5-3.7 | (t, 2H, —Si—C—C—CH$_2$—) |
| 3.8-4.1 | (d, 2H, —Si—C—C—C—O—CH$_2$—) |
| 4.1-4.4 | (d, 6H, >C=CH$_2$) |

What we claim is:

1. A fluorine-containing organosilicon compound of the general formula (I):

$$Rf-R-Si-(OCCH_3)_3 \quad \text{with } CH_2 \text{ double-bonded} \quad (I)$$

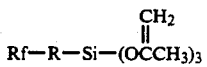

wherein Rf is a perfluoropolyether group having 3 to 17 carbon atoms, R is an alkylene group of 1 to 6 carbon atoms or a group of the formula, —R$^2$—O—R$^3$— wherein R$^2$ and R$^3$ may be the same or different and are each alkylene groups of 1-6 carbon atoms.

2. The fluorine-containing organosilicon compound as claimed in claim 1, wherein Rf in said general formula (I) is a perfluoropolyether group selected from the group consisting of the compounds having the formulas:

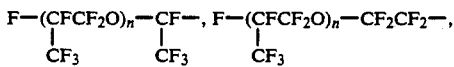

F—(CFCF$_2$O)$_n$—CF—,  F—(CFCF$_2$O)$_n$—CF$_2$CF$_2$—,
          |                    |            |
          CF$_3$                CF$_3$    CF$_3$

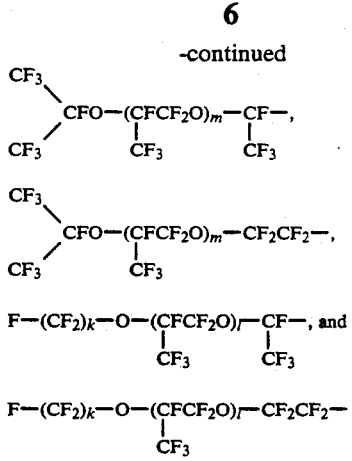

wherein n is an integer of 1 to 5, m an integer of 0 to 4, k an integer of 1 to 12 and l an integer of 1 to 7.

3. The fluorine-containing organosilicon compound as claimed in claim 1, wherein R in said general formula (I) is —CH$_2$CH$_2$—, —CH$_2$CH$_2$CH$_2$— or —CH$_2$OCH$_2$CH$_2$CH$_2$—.

4. A process of production of the fluorine-containing organosilicon compound of claim 1 comprising the step of reacting acetone in the presence of a dehydrochlorinating agent with a fluorine-containing trichlorosilane of the general formula (II):

$$Rf-R-SiCl_3 \quad (II)$$

wherein Rf and R are as defined above.

5. The process of production as claimed in claim 4, wherein said dehydrochlorinating agent comprises at least one member selected from the group consisting of triethylamine, pyridine, dimethylaniline and diethylamine.

6. The process of production as claimed in claim 4, wherein said reaction is carried out using a metal halide as a catalyst.

7. The process of production as claimed in claim 6, wherein said metal halide comprises at least one metal halide selected from the group consisting of copper chloride, aluminum chloride and zinc chloride.

* * * * *